US010508987B2

(12) United States Patent
Caine

(10) Patent No.: US 10,508,987 B2
(45) Date of Patent: Dec. 17, 2019

(54) SYSTEM AND METHOD FOR REMOTE CALIBRATION OF IRRADIANCE SENSORS OF A SOLAR PHOTOVOLTAIC SYSTEM

(71) Applicant: Also Energy, Inc., Boulder, CO (US)

(72) Inventor: Holden R. Caine, Boulder, CO (US)

(73) Assignee: Also Energy, Inc., Boulder, CO (US)

( * ) Notice: Subject to any disclaimer, the term of this patent is extended or adjusted under 35 U.S.C. 154(b) by 99 days.

(21) Appl. No.: 15/702,604

(22) Filed: Sep. 12, 2017

(65) Prior Publication Data

US 2018/0073980 A1 Mar. 15, 2018

Related U.S. Application Data

(60) Provisional application No. 62/393,470, filed on Sep. 12, 2016.

(51) Int. Cl.
| | | |
|---|---|---|
| *G01N 21/27* | (2006.01) | |
| *G01J 1/44* | (2006.01) | |
| *H02S 50/10* | (2014.01) | |
| *H02S 50/00* | (2014.01) | |
| *H02S 50/15* | (2014.01) | |
| *G01J 1/42* | (2006.01) | |

(52) U.S. Cl.
CPC ........... *G01N 21/274* (2013.01); *G01J 1/44* (2013.01); *H02S 50/00* (2013.01); *H02S 50/10* (2014.12); *H02S 50/15* (2014.12); *G01J 2001/4266* (2013.01)

(58) Field of Classification Search
CPC .......... H02S 50/00; H02S 50/10; H02S 50/15; G01N 21/274; G01J 1/40; G01J 1/44
See application file for complete search history.

(56) References Cited

U.S. PATENT DOCUMENTS

| | | |
|---|---|---|
| 3,872,286 A | 3/1975 | Putman |
| 4,280,061 A | 7/1981 | Lawson-Tancred |
| 4,752,697 A | 6/1988 | Lyons et al. |
| 5,712,572 A | 1/1998 | Tamechika et al. |

(Continued)

FOREIGN PATENT DOCUMENTS

| | | |
|---|---|---|
| WO | WO 02/25987 | 3/2002 |
| WO | WO 2006/119031 | 11/2006 |

OTHER PUBLICATIONS

"CM21 Precision Pyranometer Instruction Manual," Kipp & Zonen, 2004, version 1004, 66 pages.

(Continued)

*Primary Examiner* — Bryan Bui
(74) *Attorney, Agent, or Firm* — Sheridan Ross PC

(57) ABSTRACT

The invention provides a system and method for analyzing the performance of an irradiance sensor of a photovoltaic system. More specifically, a remote calibration system may receive irradiance data from an irradiance sensor of a PV system. The remote calibration system may then filter the irradiance data using one or more of a threshold filter, a curve fit filter, and a correlation filter. The filtered irradiance data is then compared to an estimated irradiance to generate an irradiance weighted average which may be used to adjust subsequent irradiance data provided by the irradiance sensor. A report system can be adjusted with the irradiance weighted average to prevent generation of a report for the irradiance sensor.

20 Claims, 6 Drawing Sheets

(56) References Cited

U.S. PATENT DOCUMENTS

| | | | |
|---|---|---|---|
| 6,311,137 | B1 | 10/2001 | Kurokami et al. |
| 6,425,248 | B1 | 7/2002 | Tonomura et al. |
| 7,020,566 | B2 | 3/2006 | Villicana et al. |
| 7,133,787 | B2 | 11/2006 | Mizumaki |
| 7,336,201 | B2 | 2/2008 | Green et al. |
| 7,742,897 | B2 | 6/2010 | Herzig |
| 8,106,543 | B2 | 1/2012 | Huang et al. |
| 8,115,096 | B2 | 2/2012 | Shan et al. |
| 8,269,374 | B2 | 9/2012 | De Caires |
| 8,373,312 | B2 | 2/2013 | O'Brien et al. |
| 8,682,585 | B1 | 3/2014 | Hoff |
| 8,725,437 | B2 | 5/2014 | Caine |
| 8,738,328 | B2 | 5/2014 | Herzig et al. |
| 9,660,574 | B2 * | 5/2017 | Caine .............. H02S 50/00 |
| 2002/0059035 | A1 | 5/2002 | Yagi et al. |
| 2002/0143693 | A1 | 10/2002 | Soestbergen et al. |
| 2004/0067746 | A1 | 4/2004 | Johnson |
| 2004/0103056 | A1 | 5/2004 | Ikeda et al. |
| 2004/0138977 | A1 | 7/2004 | Tomkins et al. |
| 2004/0148336 | A1 | 7/2004 | Hubbard et al. |
| 2004/0176965 | A1 | 9/2004 | Winch et al. |
| 2004/0177027 | A1 | 9/2004 | Adachi |
| 2004/0230377 | A1 | 11/2004 | Ghosh et al. |
| 2004/0236587 | A1 | 11/2004 | Nalawade |
| 2005/0004839 | A1 | 1/2005 | Bakker et al. |
| 2005/0039787 | A1 | 2/2005 | Bing |
| 2005/0131810 | A1 | 6/2005 | Garrett |
| 2006/0271214 | A1 | 11/2006 | Brown |
| 2007/0162367 | A1 | 7/2007 | Smith et al. |
| 2007/0174219 | A1 | 7/2007 | Bryan et al. |
| 2007/0203860 | A1 | 8/2007 | Golden et al. |
| 2007/0219932 | A1 | 9/2007 | Carroll et al. |
| 2007/0226163 | A1 | 9/2007 | Robles |
| 2008/0091590 | A1 | 4/2008 | Kremen |
| 2008/0091625 | A1 | 4/2008 | Kremen |
| 2008/0172256 | A1 | 7/2008 | Yekutiely |
| 2008/0215500 | A1 | 9/2008 | De La Motte |
| 2009/0177458 | A1 | 7/2009 | Hochart et al. |
| 2009/0222224 | A1 | 9/2009 | Lewis et al. |
| 2010/0174643 | A1 | 7/2010 | Schaefer et al. |
| 2010/0185337 | A1 | 7/2010 | Le Pivert |
| 2010/0219983 | A1 | 9/2010 | Peleg et al. |
| 2010/0271222 | A1 | 10/2010 | Kerrigan et al. |
| 2011/0066401 | A1 | 3/2011 | Yang et al. |
| 2011/0184583 | A1 | 7/2011 | El-Barbari et al. |
| 2011/0210610 | A1 | 9/2011 | Mitsuoka et al. |
| 2011/0282601 | A1 | 11/2011 | Hoff |
| 2012/0084027 | A1 * | 4/2012 | Caine .............. H02S 50/10 702/58 |
| 2013/0085885 | A1 | 4/2013 | Sahai et al. |
| 2013/0264884 | A1 | 10/2013 | Kuo et al. |
| 2014/0018969 | A1 | 1/2014 | Forbes |
| 2014/0188410 | A1 | 7/2014 | Kerrigan et al. |
| 2015/0012258 | A1 | 1/2015 | Caine |
| 2015/0123798 | A1 | 5/2015 | Boross et al. |
| 2015/0188415 | A1 | 7/2015 | Abido et al. |
| 2016/0190984 | A1 | 6/2016 | Caine |
| 2018/0188301 | A1 | 7/2018 | McBrearty et al. |
| 2018/0196092 | A1 | 7/2018 | McBrearty et al. |
| 2018/0196901 | A1 | 7/2018 | McBrearty et al. |

OTHER PUBLICATIONS

"Pyranometer Model SP-110 and SP-230 Owner's Manual," Apogee Instruments, Inc., 2013, 18 pages.

"PVIQ Performance Analysis," Locus Energy, Oct. 13, 11 pages [retrieved from: http://locusenergy.com/wp-content/uploads/2013/10/Locus-Energy-PVIQ-Performance-Analysis-White-Paper.pdf].

Geuder et al. Long-term Behavior, Accuracy and Drift of LI-200 Pyranometers as Radiation Sensors in Rotating Shadowband Irradiometers (RSI), Energy Procedia, Dec. 2014, vol. 49, pp. 2330-2339.

Official Action for U.S. Appl. No. 14/584,202, dated Jan. 4, 2018, 37 pages.

Chaouachi et al. "A novel multi-model neuro-fuzzy-based MPPT for three-phase grid-connected photovoltaic system," Solar Energy, 2010, vol. 84, pp. 2219-2229.

Patcharaprakiti et al. "Modeling of Photovoltaic Grid Connected Inverters Based on Nonlinear System Identification for Power Quality Analysis," Electrical Generation and Distribution Systems and Power Quality Distrurbances, InTech, Nov. 2011, vol. 21, pp. 53-82.

Notice of Allowance for U.S. Appl. No. 13/253,154, dated Jan. 6, 2014, 10 pages.

Official Action for U.S. Appl. No. 14/326,342, dated Oct. 19, 2017 32 pages.

Official Action for U.S. Appl. No. 14/584,202, dated May 18, 2017 26 pages.

Official Action for U.S. Appl. No. 14/957,374, dated Oct. 12, 2016 9 pages.

Notice of Allowance for U.S. Appl. No. 14/957,374, dated Feb. 15, 2017 7 pages.

"Atlas DCA," Peak Electronic Design, Ltd., 2008.

Burger et al., "Asset Securitisation," 2006, pp. 1-67.

Hammer et al., "Solar energy assessment using remote sensing technologies," Remote Sensing of Environment, vol. 86, 2003, pp. 423-432.

Kroposki et al., "Photovoltaic module energy rating methodology development," 25th PVSC, May 13-17, 1996, pp. 1311-1314.

Li et al., "Determining the Optimum Tilt Angle and Orientation for Solar Energy Collection Based on Measured Solar Radiance Data," International Journal of Photoenergy, vol. 2007, No. 85402, 2007, 9 pages.

Perez et al., "A New Operational Satellite-to-Irradiance Model—Description and Validation," Manuscript Submitted to Solar Energy, Apr. 2002, retrieved from http://www.asrc.cestm.albany.edu/perez/publications/Solar%20Resource%20Assessment%20and%20Modeling/Papers%20on%20Resource%20Assessment%20and%20Satellites/A%20New%20Operational%20Satellite%20irradiance%20model-02.pdf.

Wang, "The Application of Grey System Theory in Asset Securitization Project," Journal of Grey System, vol. 19, No. 3, 2007, pp. 247-256, abstract only.

Zhu et al., "Outlier identification in outdoor measurement data: effects of different strategies on the performance descriptors of photovoltaic modules," Proceedings of the 34th IEEE Photovoltaic Specialists Conference, Jun. 7-12, 2009, pp. 828-833.

Official Action for U.S. Appl. No. 13/729,066, dated Nov. 4, 2015, 6 pages. Restriction Requirement.

Official Action for U.S. Appl. No. 13/729,066, dated Mar. 11, 2016, 16 pages.

Official Action for U.S. Appl. No. 13/729,066, dated Aug. 12, 2016, 22 pages.

Official Action for U.S. Appl. No. 13/729,066, dated Jul. 3, 2017, 25 pages.

Official Action for U.S. Appl. No. 13/729,066 dated Mar. 9, 2018, 24 pages.

Official Action for U.S. Appl. No. 13/726,066 dated Dec. 3, 2018, 35 pages.

Official Action for U.S. Appl. No. 13/726,066 dated May 16, 2019, 37 pages.

* cited by examiner

SYSTEM AND METHOD FOR REMOTE CALIBRATION OF IRRADIANCE SENSORS OF A SOLAR PHOTOVOLTAIC SYSTEM

CROSS-REFERENCE TO RELATED APPLICATIONS

This application claims priority under 35 U.S.C. § 119(e) to U.S. Provisional Patent Application Ser. No. 62/393,470 filed Sep. 12, 2016 and entitled "System and Method for Remote Calibration of Irradiance Sensors of a Solar Photovoltaic System" which is incorporated herein in its entirety by reference.

FIELD

The invention relates to systems and methods for remotely calibrating irradiance sensors of solar power systems. More specifically, the present invention provides a system and method that filters data received from an irradiance sensor, compares the filtered irradiance data to modeled irradiance data that has been adjusted for local conditions, and generates a correction factor for the irradiance sensor.

BACKGROUND

Commercial and utility-scale photovoltaic ("PV") power systems ("PV systems") require a significant initial investment and ongoing maintenance effort in order to meet their performance and financial expectations over the lifetime of the system. Accordingly, it is important to accurately and timely monitor key parameters of the PV system to evaluate the performance of the PV system. By monitoring PV systems, component failures and losses caused by factors that negatively affect the efficiency of the PV system, such as soiling of solar panels, may be identified so that a financial value of the loss may be determined.

Monitoring systems for PV systems are known and described in U.S. Pat. Nos. 6,425,248, 7,336,201, 7,742,897, 8,725,437, 8,738,328, 9,660,574, U.S. Patent Application Publication No. 2016/0190984, and U.S. Patent Application Publication No. 2015/0012258 which are each incorporated herein by reference in their entirety. PV monitoring systems typically use data from sensors, such as pyranometers, reference cells, and other types of irradiance sensors, to measure sunlight received at one or more locations of a PV system. These irradiance sensors are integral to the analysis commonly utilized to maintain optimal performance in a solar PV system. Data from irradiance sensors may be used to determine a cause of a loss. For example, some PV monitoring systems can use data from irradiance sensors to distinguish between a transitory loss (such as cloud cover or snow accumulation at the PV system) and a loss which requires some action at the PV system (such as a hardware failure or soiling of the PV system).

The irradiance data can also be used to assign a financial value the loss. The financial value of the loss may further be used to determine if it is economical to perform corrective action to ensure that the PV system is operating efficiently. For some losses, it may not be economical to perform corrective action because the value of the lost energy is less than the cost of the corrective action. Determining the financial value of the loss becomes increasingly vital in remotely located PV systems where it may not be cost effective to send technicians to take action to mitigate a small loss. Accordingly, obtaining accurate measurements of irradiance at a PV system is very important to the operation and monitoring of the PV system, for correctly identifying the cause of a loss, and quantifying the value of a loss.

Unfortunately, the accuracy of irradiance sensors may deteriorate over time for a variety of reasons. For example, accuracy of irradiance sensors may be negatively influenced by the accumulation of dirt. Irradiance sensors must also be substantially level to provide accurate readings. However, irradiance sensors frequently move out of level over time decreasing the accuracy of data collected. Further, on-site irradiance sensors, such as pyranometers, that provide irradiance data for PV systems are known to become less accurate over time due to deterioration and equipment failure. Some known pyranometers decrease in accuracy by 3 percent or more annually. Accordingly, irradiance sensors require frequent on-site maintenance or calibration by the manufacturer. It is not uncommon to return irradiance sensors to their manufacturer every 1 or 2 years.

The calibration of irradiance sensors often requires removal of the sensor and re-installation after it has been calibrated. Occasionally, irradiance sensors that are out of calibration by greater than a predetermined amount may be replaced. Sending technicians to inspect, calibrate, and/or replace irradiance sensors frequently requires a substantial cost in labor because PV systems are often remotely located.

Some methods of calibrating irradiance sensors include comparing the performance of the irradiance sensor to a reference irradiance sensor in an indoor facility. Some suppliers of irradiance sensors recommend factory calibration at least every two years. One manufacturer claims calibration can usually be completed within four weeks, although urgent calibration can be performed in three weeks or less. As one of skill in the art will appreciate, the performance of PV systems cannot be accurately monitored without an irradiance sensor for such a long period of time. Accordingly, a temporary irradiance sensor must frequently be installed at the PV system during calibration of an irradiance sensor, further increasing the cost and labor expense associated with maintaining the irradiance sensor. Of course, after a recalibrated irradiance sensor is returned from a factory calibration, a technician must make another trip to a remote PV system to remove the temporary irradiance sensor and reinstall the recalibrated irradiance sensor, incurring more labor and travel expenses. As solar PV systems are generally expected to operate for 20 years or more, the calibration of irradiance sensors requires considerable labor and associated expense during the operational life of the PV system, especially when the PV system is located in a remote area.

Due to the known deficiencies and inherent deterioration of the accuracy of irradiance sensors, some PV system operators install additional irradiance sensors at PV system. Other operators of PV systems schedule periodic on-site maintenance and/or replacement of their irradiance sensors. As can be appreciated, both of these actions further increase the expense associated with a PV system.

Thus, there is a need for a system and method that can analyze the performance of an irradiance sensor and compensate for drift of the irradiance sensor while requiring minimal, or no, capital and equipment investment. The system and methods of the present invention can also adjust a report system to prevent unnecessary reports or alarms for an irradiance sensor which is out of specification but which provides irradiance data which may be corrected by use of a correction factor.

SUMMARY OF THE INVENTION

In accordance with the invention, a remote calibration a system and method are provided for remotely calibrating irradiance sensors. The system and method described herein can be employed to remotely determine performance of an irradiance sensor. After determining the performance of the irradiance sensor, the data from the irradiance sensor may be adjusted to compensate for a difference between irradiance measured by the irradiance sensor and an estimated irradiance at the site of the irradiance sensor. In this manner, the system and method can adjust the data received from the irradiance sensor to compensate for drift or other sources of error of the irradiance sensor.

In one embodiment, the remote calibration system generates a correction factor to adjust raw irradiance data received from the irradiance sensor. Optionally, the remote calibration system may use the correction factor to adjust a report system such that the irradiance sensor is not reported as being faulty. By adjusting the report system, the remote calibration system provides a more accurate reporting status for an irradiance sensor. More specifically, adjusting the report system to account for a correction factor associated with an irradiance sensor providing irradiance data that is useable after being adjusted by the correction factor prevents reports indicating that the irradiance sensor is faulty or in need of maintenance that otherwise would be generated by the report system. More specifically, when an irradiance sensor is out of calibration but raw irradiance data from the irradiance sensor is usable after being adjusted with a correction factor generated by the remote calibration system, the irradiance sensor does not require inspection or maintenance and the report system should not generate a report indicating that the irradiance sensor is faulty or in need of maintenance or inspection. Accordingly, the remote calibration system prevents unnecessary trips by technicians to remote PV system when irradiance sensors do not require inspection, adjustment, or maintenance. One of skill in the art will appreciate that by preventing unnecessary travel by technicians, the present remote calibration system saves associated labor and travel expenses.

One aspect of the present invention is a system and method that uses an atmospheric model of sunlight for any location on the planet, along with data filtering and other techniques, to measure the performance of an irradiance sensor, such as, but not limited to, a pyranometer. The measured performance may comprise a correction factor. The correction factor may be used to adjust data received from the irradiance sensor to compensate for drift or other sources of error. Alternatively, the correction factor may provide an indication that the irradiance sensor should be inspected, recalibrated, or replaced. In one embodiment, the correction factor is used to alter a report system associated with the pyranometer to prevent reports for pyranometers that generate irradiance data which can be used after compensating for drift or other error. Optionally, when the correction factor is above a predetermined amount, a report system may generate a report which indicates that the irradiance sensor should be inspected, recalibrated, or replaced. In one embodiment, if the correction factor is greater than 3%, the report system generates a report indicating the irradiance sensor should be inspected, recalibrated, or replaced.

Another aspect is to use a ratio of measured irradiance and an estimated irradiance to calculate a correction factor to compensate for error of an irradiance sensor due to degradation, soiling, or for other factors. The estimated irradiance may be determined using one or more known blue-sky models. In one embodiment, the estimated irradiance is received from a remote system over a network. For example, the estimated irradiance may be received from a third party or internet site. Optionally, the estimated irradiance may be adjusted by one or more external measurements of temperature, humidity, air pollution or other site characteristics at the location of the PV system.

In one embodiment, the measured irradiance is filtered by one or more of a threshold filter, a curve fit filter, and a correlation filter. Accordingly, in one embodiment, the measured irradiance may be compared to a minimum irradiance threshold value to determine if a data point is affected by an environmental factor (such as clouds, snow, airborne particulate matter, temperature, humidity, or season) at the PV system. In another embodiment, the measured irradiance is fit to a second order polynomial curve (or similar). The quality of the fit of the measured irradiance is then evaluated to determine if the data point is affected by the environmental factor. In still another embodiment, the correlation of the measured irradiance to the estimated irradiance is evaluated to determine if the data point is affected by the environmental factor.

Another aspect of the present invention is the use of irradiance-weighted averages to more strongly consider data points of measured irradiance during periods of high irradiance.

It is still another aspect of the present invention to save a correction factor generated from one or more days of data. The correction factor may subsequently be used to correct (or adjust) irradiance measurements. In one embodiment, the correction factor may be used to adjust PV system performance models or PV system performance ratios. In another embodiment, the correction factor is used by a PV monitoring system to alter alarms or reports associated with an irradiance sensor. More specifically, if the correction factor is below a predetermined amount, the PV monitoring system will not generate a report indicating that the irradiance sensor is out of calibration or that the irradiance sensor requires calibration. When the correction factor is equal to or above the predetermined amount, the PV monitoring system will generate a report indicating that the irradiance sensor should be calibrated, inspected, or replaced.

Yet another aspect of the present invention is to use an irradiance weighted average to correct one or more of global horizontal irradiance (GHI) data, plane of array (POA), and direct normal irradiance (DNI) data for a PV system.

One aspect of the present invention is to provide a system for analyzing and calibrating irradiance sensors. The system generally includes, but is not limited to: (1) a memory; and (2) a processor in communication with the memory. The processor is programmed to: (a) receive irradiance data from an irradiance sensor of a PV system; (b) generate an estimated irradiance for the PV system; (c) filter the received irradiance data; and (d) generate an irradiance weighted average for the irradiance sensor.

In one embodiment, filtering the received irradiance data comprises analyzing the irradiance data using one or more of a threshold filter, a curve fit filter, and a correlation filter. In another embodiment, generating the irradiance weighted average comprises comparing data $M_t$ from the irradiance sensor to the estimated irradiance $b_t$ using the formula:

$$\frac{\sum (b_t * M_t)}{\sum (b_t)}$$

Another aspect of the invention is a method of analyzing and calibrating irradiance sensors. The method comprises: (1) receiving irradiance data from an irradiance sensor of a PV system; (2) generating an estimated irradiance for the PV system; (3) filtering the received irradiance data; and (4) generating an irradiance weighted average for the irradiance sensor. Optionally, the method may further comprise adjusting irradiance data from the irradiance sensor by the irradiance weighted average. In another embodiment, the method includes generating a report for a user, the report comprising one or more of a graph and an image presented on a display.

It is yet another aspect of the present invention to provide a non-transitory computer readable medium having stored thereon computer-executable instructions executable by a processor of a remote calibration system, the computer-executable instructions causing the processor to execute a method of analyzing performance of an irradiance sensor. The instructions include, but are not limited to: (1) an instruction to receive irradiance data from an irradiance sensor of a PV system; (2) an instruction to generate an estimated irradiance for the PV system; (3) an instruction to filter the received irradiance data; and (4) an instruction to generate an irradiance weighted average for the irradiance sensor.

Optionally, in one embodiment, the instruction to filter further comprises an instruction to analyze the irradiance data with one or more of a threshold filter, a curve fit filter, and a correlation filter. In another embodiment, the instructions comprise one or more of: (a) an instruction to generate a report to inspect the irradiance sensor; and (b) an instruction to generate a report to calibrate the irradiance sensor.

Another aspect is a report system for a PV system. The report system is operable to provide information about the status of the PV system and performance of components of the PV system. In one embodiment, the report system can generate a report including information about the operation of an irradiance sensor associated with the PV system. The report can include information about the accuracy of the irradiance sensor. The information may include an irradiance weighted average calculated to correct an error of the irradiance sensor.

In one embodiment, the report system can adjust settings used by the report system to determine when to send a report. More specifically, the report system can modify the settings to account for the irradiance weighted average. In this manner, in one embodiment, the report system will not send a report listing the irradiance sensor as faulty when data from the irradiance sensor is usable after being adjusted with the correction factor. Alternatively, if the irradiance weighted average cannot correct an error in data from the irradiance sensor, the report system can generate an alarm. In one embodiment, the alarm can indicate that the irradiance sensor is faulty. Additionally, or alternatively, the alarm can also indicate that the irradiance sensor requires on-site inspection or maintenance. Optionally, the report system can include a cause or reason for the error in the data from the irradiance sensor. More specifically, the alarm can indicate that the irradiance sensor is out of alignment.

In one embodiment, the report system can send an alarm when the irradiance weighted average indicates the irradiance sensor is more than a predetermined amount out of calibration. Optionally, the predetermined amount may be preset or set by an operator. In one embodiment, the predetermined amount is 3%.

Another aspect of the present invention is a method of analyzing and calibrating an irradiance sensor of a PV system. The method comprises: (1) estimating irradiance at the PV system; (2) receiving irradiance data from the irradiance sensor; (3) filtering the received irradiance data; and (4) generating an irradiance weighted average for the irradiance sensor. Optionally, the method can further include adjusting irradiance data from the irradiance sensor by the irradiance weighted average.

In one embodiment, the method further comprises generating a report for a user. The report can include one or more of a graph and an image presented on a display. The report may include information about the irradiance sensor, such as the irradiance weighted average. In one embodiment, a threshold associated with the report is adjusted to account for the irradiance weighted average. In this manner, the report is not generated if data from the irradiance sensor can be corrected using the irradiance weighted average. Alternatively, in one embodiment, if data from the irradiance sensor includes an error that cannot be corrected with the irradiance weighted average, the report can indicate that the irradiance sensor is faulty. In one embodiment, the report may indicate that the irradiance sensor should be inspected or adjusted. Optionally, the report may include a cause of the error in the data from the irradiance sensor. For example, the report may indicate that the irradiance sensor is out of alignment.

In another embodiment, filtering the received irradiance data comprises analyzing the irradiance data using one or more of a threshold filter, a curve fit filter, and a correlation filter.

In one embodiment, generating the irradiance weighted average comprises comparing data $M_t$ from the irradiance sensor to the estimated irradiance $b_t$ using the formula:

$$\frac{\sum (b_t * M_t)}{\sum (b_t)}$$

Still another aspect is a system for analyzing and calibrating an irradiance sensor of a PV system. The system includes, but is not limited to: (1) a memory; and (2) a processor in communication with the memory, the processor programmed to: (i) receive an estimated irradiance for the PV system; (ii) receive irradiance data from the irradiance sensor of the PV system; (iii) filter the received irradiance data; and (iv) generate an irradiance weighted average for the irradiance sensor. The processor can be further programmed to adjust irradiance data from the irradiance sensor with the irradiance weighted average.

In one embodiment, the system further includes one or more of: a photovoltaic string to convert sunlight into electrical energy; a combiner to combine DC power from a plurality of photovoltaic strings; an inverter for converting DC power from a plurality of combiners into AC power; and a sensor to detect environmental conditions at the PV system.

Optionally, the processor is further programmed to modify a report module using the irradiance weighted average. In one embodiment, modifying the report module prevents generation of a report associated with the irradiance sensor when irradiance data from the irradiance sensor can be corrected using the irradiance weighted average. In another embodiment, the processor is further programmed to generate a report from the report module when data from the irradiance sensor cannot be corrected with the irradiance weighted average. Optionally, the report module generates a report when the irradiance weighted average indicates the irradiance sensor is out of calibration by greater than a predetermined amount. In one embodiment, the predetermined amount is pre-set. Alternatively, a user may enter the predetermined amount. In one embodiment, the predetermined amount is 3 percent.

In one embodiment, the processor is further programmed to determine a reason irradiance data from the irradiance sensor is different from the estimated irradiance. Optionally, the processor uses the irradiance weighted average to determine at least one of: (a) the irradiance sensor is damaged; and (b) the irradiance sensor is out of alignment. In one embodiment, the processor is programmed to determine the irradiance sensor is damaged when the irradiance weighted average changes at greater than a predetermined rate. In another embodiment, the processor is programmed to determine the irradiance sensor is out of alignment when a difference between the received irradiance data and the estimated irradiance varies based on a position of the sun. Optionally, the processor is further programmed to generate a report with the report module after determining the irradiance sensor is damaged or is out of alignment. The report can indicate that the irradiance sensor needs on-site inspection.

Another aspect is a non-transitory computer readable medium having stored thereon computer-executable instructions executable by a processor of a remote calibration system, the computer-executable instructions causing the processor to execute a method of analyzing performance of an irradiance sensor of a PV system. The instructions include, but are not limited to, one or more of: (1) an instruction to generate an estimated irradiance for the PV system; (2) an instruction to receive irradiance data from the irradiance sensor of the PV system; (3) an instruction to filter the received irradiance data using the estimated irradiance; and (4) an instruction to generate an irradiance weighted average for the irradiance sensor.

In one embodiment, the instruction to filter further comprises an instruction to compare the irradiance data with estimated irradiance using one or more of a threshold filter, a curve fit filter, and a correlation filter.

Optionally, the instructions may further include an instruction to generate a report. The instruction to generate a report may include an instruction to generate a report when data from the irradiance sensor cannot be corrected with the irradiance weighted average. In one embodiment, the instructions to generate a report include adjusting a threshold which triggers the report. More specifically, in one embodiment, the threshold is adjusted with the irradiance weighted average. In this manner, the trigger is adjusted such that a report is not generated when an error in data received from the irradiance sensor can be corrected with the irradiance weighted average. Optionally, the report may indicate that the irradiance sensor is faulty. In one embodiment, the report may recommend inspection of the irradiance sensor. In another embodiment, the report may recommend calibration of the irradiance sensor. In still another embodiment, the report may indicate a cause of the error in the data from the irradiance sensor, such as that the irradiance sensor is out of alignment.

There are numerous advantages to the remote calibration systems and methods of the present invention. The remote calibration system and method may be used to generate a correction factor to adjust raw irradiance data received from an irradiance sensor such that resulting corrected data may be used without replacing or physically adjusting the irradiance sensor. Existing weather service data can be used to generate the correction factor. Obtaining existing weather service data does not substantially increase the cost or complexity of the system, yet provides an economical solution to known and inherit shortcomings of irradiance sensors.

Another benefit of present systems and methods is that irradiance sensors, such as on-site pyranometers, can be used for longer periods of time without replacement or maintenance. In this manner, the systems and methods of the present disclosure decrease or delay hardware replacement and maintenance expenses associated with irradiance sensors.

A correction factor for an irradiance sensor generated as described herein can also be used to adjust a report system associated with the irradiance sensor. By adjusting the report system to take into consideration a known error of an irradiance sensor, the invention substantially improves the report system which otherwise would generate unnecessary or inaccurate reports related to the irradiance sensor.

In some embodiments, the remote calibration systems and methods of the present invention use existing weather service data and data currently received from irradiance sensors in a new way to determine a correction factor. No new sensors at the PV system are required to determine the correction factor. Thus, the remote calibration systems and methods of this disclosure do not require additional hardware installation at the site of the PV system or labor costs associated with installing additional hardware and sensors.

An additional benefit of the systems and methods is the ability to determine an amount of error associated with raw irradiance data received from an irradiance sensor. If a correction factor generated by the remote calibration system can compensate for error associated with the raw irradiance data, data from the irradiance sensor may be used to monitor the PV system without costly replacement or maintenance. Accordingly, the correction factor may be used to adjust reports generated by PV monitoring systems. If the correction factor is above a predetermined amount, the error associated with the raw irradiance data may be too great to be reliably used even after compensation with the correction factor. In this case, the remote calibration system may determine that the irradiance sensor requires inspection, maintenance, or calibration. A report may then be sent to a user which indicates that the irradiance sensor should be inspected.

Accordingly, in one embodiment, the systems and methods disclosed automatically monitor an irradiance sensor and adjust raw data received from the irradiance sensor. The systems and methods do not require costly additional sensors and facilitate monitoring of PV systems while reducing the frequency and costs of maintenance and inspection. The systems and methods also automatically make timely decisions to alter report system to prevent unnecessary reports which could generate trips by technicians to a remote PV system. For example, for an irradiance sensor which is out of calibration but for which a correction factor may be used to compensate the raw irradiance data, the system and method will alter logic of a report system to prevent generation and transmission of a report that the irradiance sensor is out of calibration. If the irradiance sensor is out of calibration such that the correction factor will not adequately compensate the raw irradiance data, the system and method can send a report indicating that the irradiance sensor is faulty or out of calibration and requires one or more of inspection and maintenance. Thus, the present disclosure reduces costs associated with operating PV systems.

In one embodiment, the system and method may use a correction factor generated for an irradiance sensor to determine if the cost of sending maintenance personnel to inspect the irradiance sensor is economical. More specifically, an hourly cost associated with a technician may be used by the remote calibration system to estimate a cost of inspecting the irradiance sensor. The remote calibration system may consider time required for the technician to travel to and from the irradiance sensor as well as time required to inspect and/or replace the irradiance sensor. If the cost of inspecting the irradiance sensor is greater than a predetermined amount, the remote calibration system may determine it is not cost effective to send a technician to the irradiance sensor.

Optionally, the remote calibration system may send a report indicating that the irradiance sensor is out of calibration but that the irradiance sensor does not currently require a visit by a technician. The remote calibration system may also add inspection and maintenance of the irradiance sensor to a report or task list for a subsequent visit by a technician to a PV system associated with the irradiance sensor. In this manner, the remote calibration system can prevent an unscheduled, and unnecessary, trip by a technician to a remote PV system when the irradiance sensor is functioning adequately, although out of specification, when the correction factor adequately compensates for error in the raw irradiance data.

References made herein to "photovoltaic arrays," "photovoltaic systems," "photovoltaic modules," or "solar panels," should not necessarily be construed as limiting the invention to a particular type of solar power system. It will be recognized by one skilled in the art that the present invention may be used to analyze and remotely calibrate irradiance sensors used in any type of application.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium," as used herein, refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the invention is considered to include a tangible storage medium or distribution medium and prior art-recognized equivalents and successor media, in which the software implementations of the invention are stored. It should be noted that any computer readable medium that is not a signal transmission may be considered non-transitory.

The term "desktop," as used herein, refers to a metaphor used to portray systems. A desktop typically includes pictures, called icons, that show applications, windows, cabinets, files, folders, documents, and other graphical items. The icons are generally selectable through user interface interaction to allow a user to execute applications or conduct other operations.

The term "display", as used herein, refers to a portion of a display image used to display the output of a computer to a user.

The term "displayed image", as used herein, refers to an image produced on the display. A typical displayed image is a window or desktop. The displayed image may occupy all or a portion of the display.

The term "module," as used herein, refers to any known or later developed hardware, software, computer readable medium, firmware, artificial intelligence, fuzzy logic, or combination of hardware and software with functionality associated with a particular task and that is capable of performing the functionality associated with that task.

The term "window", as used herein, refers to a, typically rectangular, displayed image on part of a display that contains or provides content different from the rest of the screen.

The terms "determine", "calculate" and "compute," and variations thereof, as used herein, are used interchangeably and include any type of methodology, process, mathematical operation or technique.

It shall be understood that the term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The preceding is a simplified summary of the invention to provide an understanding of some aspects of the invention. This summary is neither an extensive nor exhaustive overview of the invention and its various aspects, embodiments, and/or configurations. It is intended neither to identify key or critical elements of the invention nor to delineate the scope of the invention but to describe selected concepts of the invention in a simplified form as an introduction to the more detailed description presented below. As will be appreciated, other aspects, embodiments, and/or configurations of the invention are possible utilizing, alone or in combination, one or more of the features set forth above or described in detail below.

Other features and advantages of the invention will become apparent from a review of the following detailed description, taken in conjunction with the drawings.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

The following detailed description describes one or more embodiments of the disclosed system and method. First, the detailed description provides a description of a network system and a computer system that may be used in connection with the remote calibration system and method disclosed herein. The detailed description then provides a disclosure of embodiments of the remote calibration system and method disclosed herein.

Figure 1:
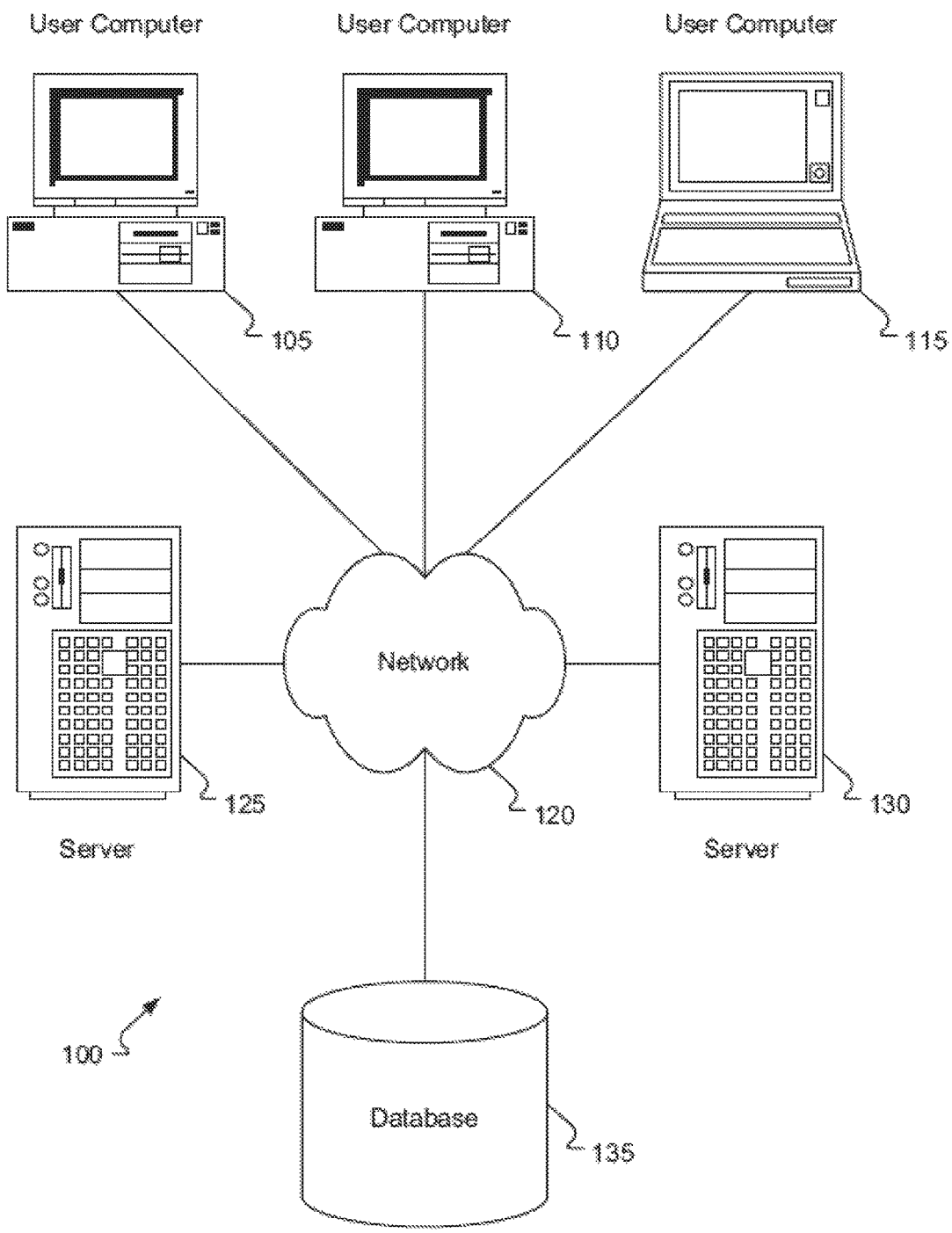
FIG. 1 is an example communications/data processing network system that may be used in conjunction with embodiments of the invention.

Referring to FIG. 1, an example network system 100 is provided that may be used in connection with a remote calibration system and method disclosed herein. More specifically, FIG. 1 illustrates a block diagram of a system 100 that may analyze the performance of an irradiance sensor, such as a pyranometer, to calculate sensor drift or other errors in data from the irradiance sensor and subsequently recalibrate the irradiance sensor. The system 100 generally includes one or more data processors, such as user computers 105, 110, and 115. The user computers 105, 110, and 115 may be general purpose personal computers (including, merely by way of example, personal computers and/or laptop computers running various versions of Microsoft Corp.'s and/or Apple Corp.'s operating systems, such as MS Windows™, Macintosh™, or iOS) and/or workstation computers running any of a variety of commercially-available UNIX™ or UNIX-like operating systems. These user computers 105, 110, 115 may also have any of a variety of applications, including for example, database client and/or server applications, and web browser applications. Alternatively, the user computers 105, 110, and 115 may be any other electronic device, such as a thin-client computer, internet-enabled mobile telephone, and/or personal digital assistant, capable of communicating via a network (e.g., the network 120 described below) and/or displaying and navigating web pages or other types of electronic documents. Although the exemplary system 100 is shown with three user computers, any number of user computers may be supported.

System 100 further includes a network 120. The network 120 may be any type of network familiar to those skilled in the art that can support data communications using any of a variety of commercially-available protocols, including without limitation TCP/IP, SNA, IPX, AppleTalk, and the like. Merely by way of example, the network 120 may be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth™ protocol known in the art, and/or any other wireless protocol); and/or any combination of these and/or other networks.

The system may also include one or more server computers 125, 130. One server may be a web server 125, which may be used to process requests for web pages or other electronic documents from user computers 105, 110, and 120. The web server can be running an operating system including any of those discussed above, as well as any commercially-available server operating systems. The web server 125 can also run a variety of server applications, including HTTP servers, FTP servers, CGI servers, database servers, Java servers, and the like. In some instances, the web server 125 may publish operations available as one or more web services.

The system 100 may also include one or more file and/or application servers 130, which can, in addition to an operating system, include one or more applications accessible by a client running on one or more of the user computers 105, 110, 115. The server(s) 130 may be one or more general purpose computers capable of executing programs or scripts in response to the user computers 105, 110 and 115. As one example, the server may execute one or more web applications. The web application may be implemented as one or more scripts or programs written in any programming language, such as Java™, C, C#™ or C++, and/or any scripting language, such as Perl, Python, or TCL, as well as combinations of any programming/scripting languages. The application server(s) 130 may also include database servers, including without limitation those commercially available from Oracle, Microsoft, Sybase™, IBM™ and the like, which can process requests from database clients running on a user computer 105.

In some embodiments, an application server 130 may create web pages dynamically for displaying information and reports generated by the remote calibration system. The web pages created by the web application server 130 may be forwarded to a user computer 105 via a web server 125. Similarly, the web server 125 may be able to receive web page requests, web services invocations, and/or input data from a user computer 105 and can forward the web page requests and/or input data to the web application server 130.

In further embodiments, the server 130 may function as a file server. Although for ease of description, FIG. 1 illustrates a separate web server 125 and file/application server 130, those skilled in the art will recognize that the functions described with respect to servers 125, 130 may be performed by a single server and/or a plurality of specialized servers, depending on implementation-specific needs and parameters.

The system 100 may also include a database 135. The database 135 may reside in a variety of locations. By way of example, database 135 may reside on a storage medium local to (and/or resident in) one or more of the computers 105, 110, 115, 125, 130. Alternatively, it may be remote from any or all of the computers 105, 110, 115, 125, 130, and in communication (e.g., via the network 120) with one or more of these. In a particular set of embodiments, the database 135 may reside in a storage-area network ("SAN") familiar to those skilled in the art. Similarly, any necessary files for performing the functions attributed to the computers 105, 110, 115, 125, 130 may be stored locally on the respective computer and/or remotely, as appropriate. In one set of embodiments, the database 135 may be a relational database, such as Oracle 10i™, that is adapted to store, update, and retrieve data in response to SQL-formatted commands.

Figure 2:
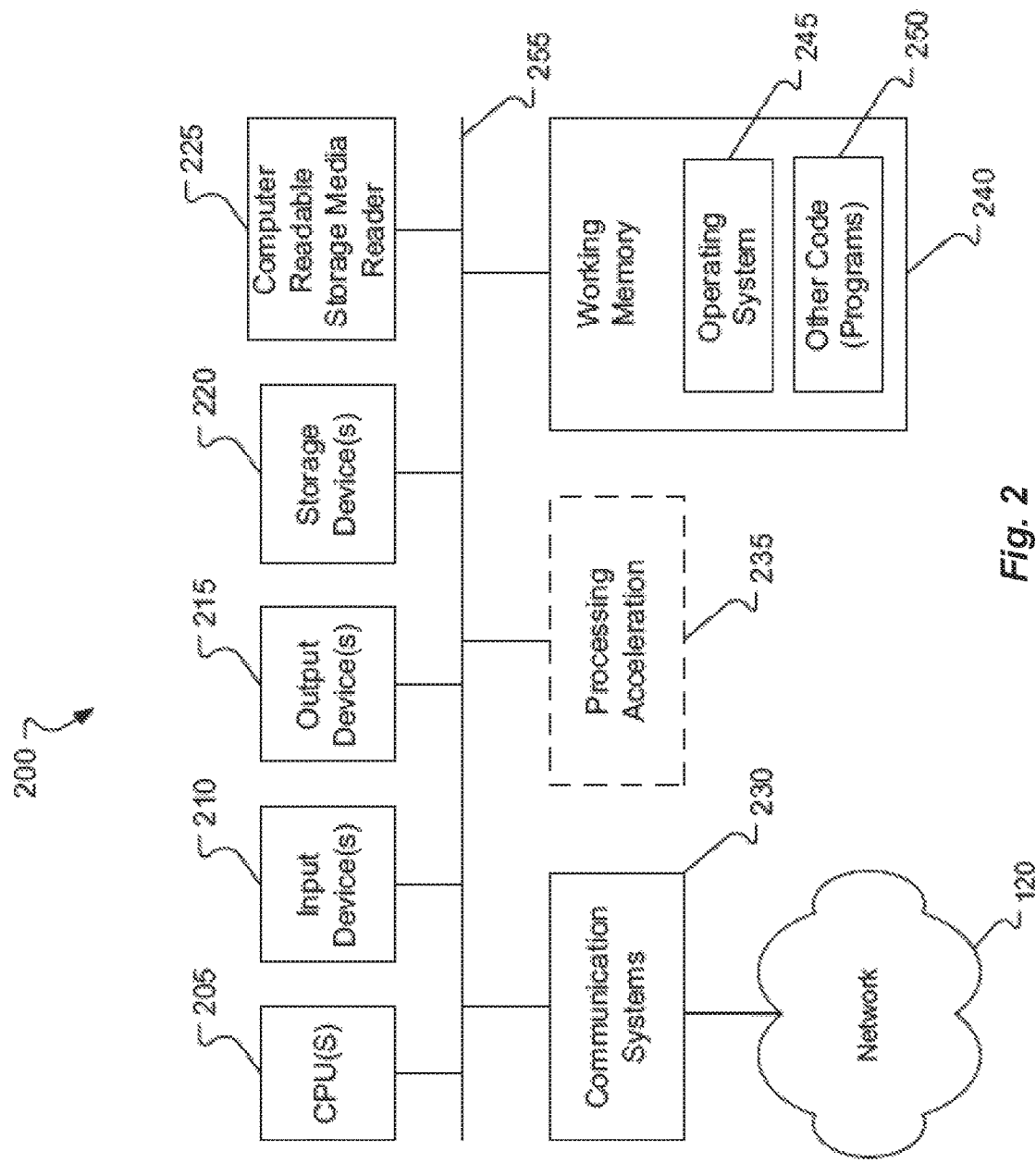
FIG. 2 is an example data processing system that may be used in conjunction with embodiments of the invention.

Referring to FIG. 2, an example data-processing system 200 is provided that may be used in connection with the remote calibration system and method disclosed herein. More specifically, FIG. 2 illustrates one embodiment of a data-processing system 200 upon which the remote calibration system or components of a remote calibration system may be deployed or executed. The data-processing system 200 is shown comprising hardware elements that may be electrically coupled via a bus 255. The hardware elements may include one or more central processing units (CPUs) 205; one or more input devices 210 (e.g., a mouse, a keyboard, etc.); and one or more output devices 215 (e.g., a display device, a printer, etc.). The data-processing system 200 may also include one or more storage devices 220. By way of example, storage device(s) 220 may be disk drives, optical storage devices, solid-state storage device such as a random access memory ("RAM") and/or a read-only memory ("ROM"), which can be programmable, flash-updateable and/or the like.

The data-processing system 200 may additionally include a computer-readable storage media reader 225; a communications system 230 (e.g., a modem, a network card (wireless or wired), an infra-red communication device, etc.); and working memory 240, which may include RAM and ROM devices as described above. In some embodiments, the data-processing system 200 may also include a processing acceleration unit 235, which can include a DSP, a special-purpose processor and/or the like.

The computer-readable storage media reader 225 can further be connected to a computer-readable storage medium, together (and, optionally, in combination with storage device(s) 220) comprehensively representing remote, local, fixed, and/or removable storage devices plus storage media for temporarily and/or more permanently containing computer-readable information. The communications system 230 may permit data to be exchanged with the network 120 and/or any other data-processing described above with respect to the system 100.

The data-processing system 200 may also comprise software elements, shown as being currently located within the working memory 240, including an operating system 245 and/or other code 250, such as program code implementing a remote calibration system or components of a remote calibration system. It should be appreciated that alternate embodiments of a data-processing system 200 may have numerous variations from that described above. For example, customized hardware might also be used and/or particular elements might be implemented in hardware, software (including portable software, such as applets), or both. Further, connection to other computing devices such as network input/output devices may be employed.

Figure 3:
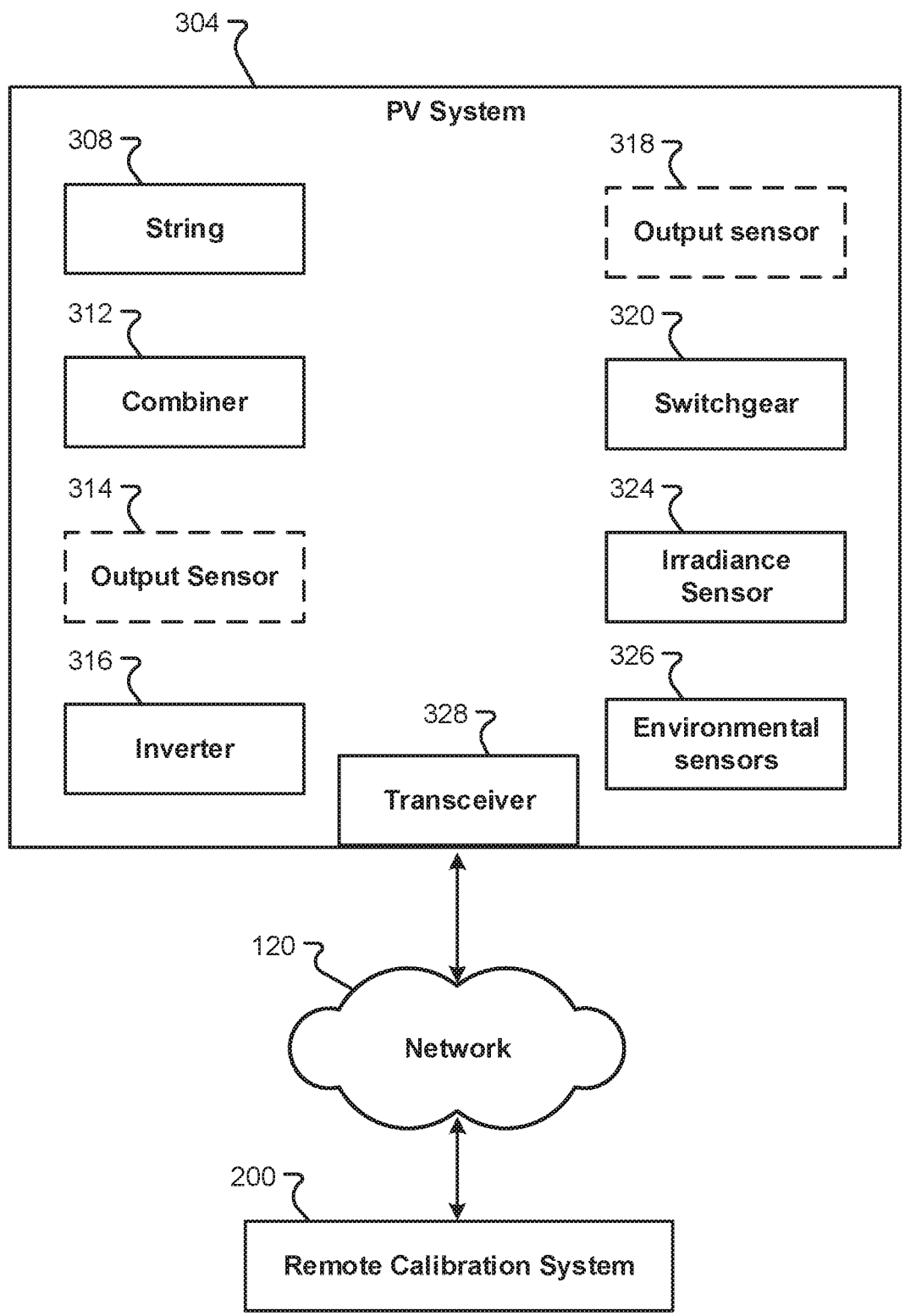
FIG. 3 is a block diagram of a PV system in communication with a remote calibration system of the present invention.

Referring now to FIG. 3, a block diagram of a PV system 304 is generally illustrated. The PV system 304 generally includes a plurality of PV strings 308, combiners 312, inverters 316, switchgear 320, an irradiance sensor 324, environmental sensors 326, and a transceiver 328. Optionally, the PV system 304 can also include one or more of output sensors 314, 318.

Each PV string 308 consists of individual solar panels, typically eight to twelve panels, wired in series. The output signals of the PV strings 308 are wired, in parallel, into the combiners 312. Each combiner 312 can receive output signals from one or more PV string 308. Each combiner 312 sums the data signals of its PV strings 308, thereby providing a cumulative direct current ("DC") power output that is associated with a plurality of PV strings 308. Optionally, an output sensor 314 can be associated with one or more of the combiners 312. The output sensor 314 can detect and report the DC power output by a combiner 312.

The output signals of the combiners 312 are wired into the inverter 316. Although only one inverter 316 is illustrated in the PV system 304, in large PV systems, multiple inverters are employed, each accepting the output signals of multiple combiners. The inverter 316 converts the DC power of the solar panels 308 into three phase alternating current ("AC") power which ultimately can be used by commercial power systems. The PV system can optionally include an output sensor 318 to measure the AC power output by the inverter 316. The three phase AC power leaves the inverter 316 and is wired into the switchgear 320 of the PV system 304 where the AC output of the PV system 304 is matched to supply power to the facility or to a utility grid.

PV systems 304 typically include at least one irradiance sensor 324. The PV system 304 may also include environmental sensors 326 to measure environmental conditions at the PV system 304. The environmental sensors 326 may include one or more sensors to measure temperature, pressure, humidity, air quality (such as levels of pollution or particulate matter in the air), wind speed, and cloud cover. The sensors 324, 326 are in communication with a transceiver 328, which transmits the sensor data through the network 120 to the remote calibration system 200.

Figure 4:
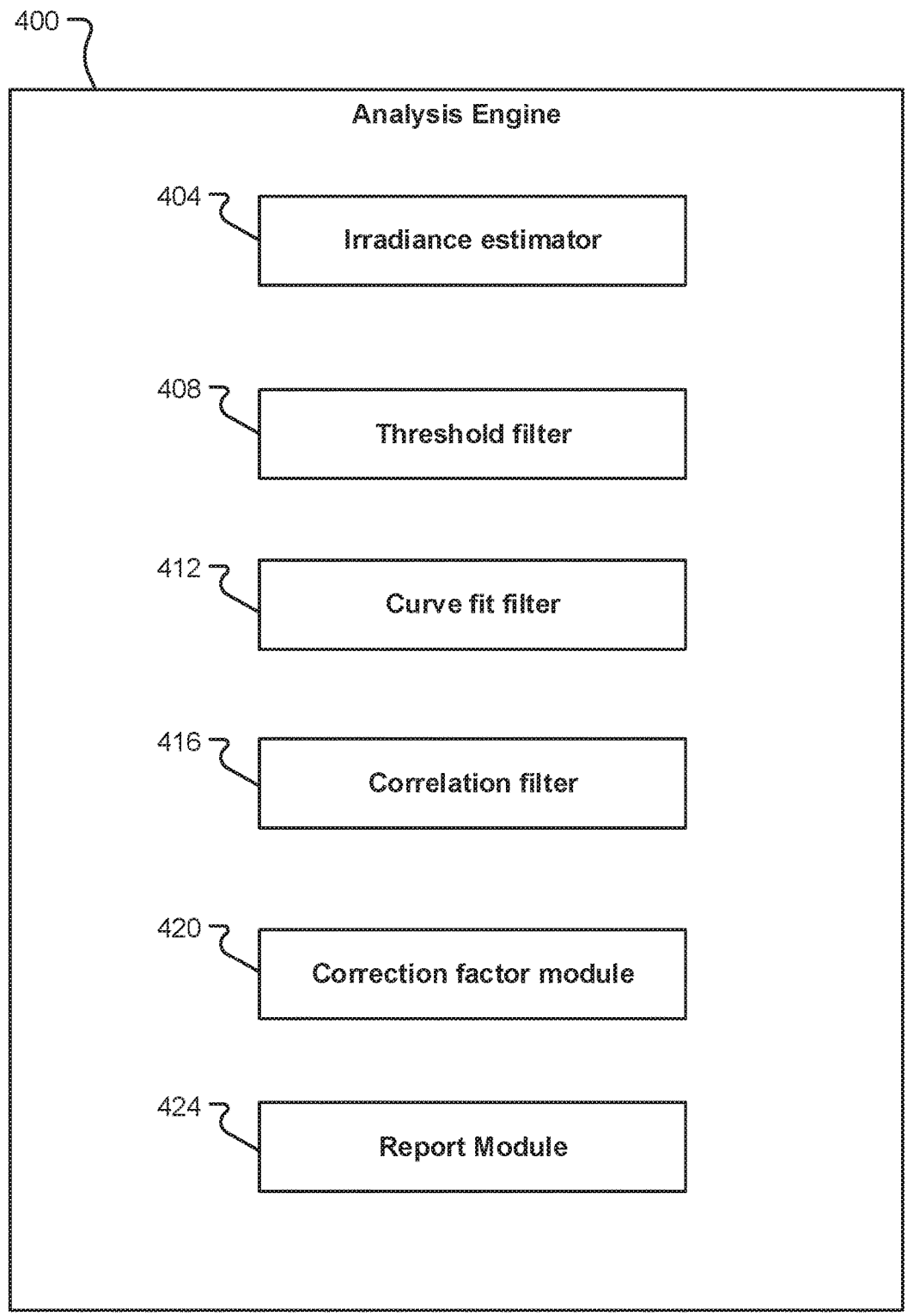
FIG. 4 is a block diagram of an analysis engine of an embodiment of the present invention.

Referring now to FIG. 4, an analysis engine 400 of one embodiment of the present invention is illustrated. The analysis engine 400 may include one or more of an irradiance estimator 404, a threshold filter 408, a curve fit filter 412, a correlation filer 416, a correction factor module 420, and a report module 424. As described above, modules and filters may be a computer readable medium with functionality associated with a particular task. Thus, one or more components 404-424 of the analysis engine 400 may comprise commands or instructions 250 stored in working memory 240 that are executable by processor 205. Additionally, or alternatively, in another embodiment, some or all of components 404-424 of the analysis engine 400 may be implemented by hardware of the system 200.

The irradiance estimator 404 determines an estimated irradiance for the PV system 304. A variety of well-established models, known as "blue-sky" models, exist for estimating irradiance at any point on the Earth for any date or time of day based on the location of the PV system 304 and considering latitude, longitude, elevation, time of day, and date of year. Many of these blue-sky models incorporate: (a) distance from the sun; (b) location of the PV system 304; and (c) air mass. The distance from the sun varies daily and affects the irradiance above the atmosphere. The location of the PV system 304 determines the amount of atmosphere that sunlight must pass through to reach the PV system 304.

Air mass affects the amount of scattering that occurs as sunlight passes through the atmosphere to the PV system 304. Optionally, the irradiance estimator 404 may receive the estimated irradiance from an external source over the network 120. Data from an external source may be freely available or obtained with a subscription. One example of a known blue-sky model is available at http://clearskycalculator.com/pyranometer.htm.

Optionally, the irradiance estimator 404 may adjust the estimated irradiance based on environmental conditions at the PV system 304. In this manner, the irradiance estimator 404 may use data received from the environmental sensors 326 to adjust the estimated irradiance to account for one or more of humidity, atmospheric pressure, temperature, cloud cover, snow cover, and air pollution detected at the PV system 304. The irradiance estimator 404 may also apply a seasonal correction to the estimated irradiance. The seasonal correction may be determined based on analysis of local conditions at the PV system 304 over a long period of time to account for local variances in irradiance. The irradiance estimator 404 may also use weather data received from a network connection 120 to a remote weather service. More specifically, many companies, and some government agencies, make weather data available over network connections, such as the internet, for a variety of locations. The communication system 230 of data-processing system 200 may connect to a remote weather service to obtain such weather data for a location proximate to the PV system 304.

The threshold filter 408 compares irradiance data received from the irradiance sensor 324 of the PV system 304 to the estimated irradiance received from the irradiance estimator 404. More specifically, the communications system 230 of data-processing system 200 receives irradiance data of an irradiance sensor 324 from the remote PV system 304 over network 120. The threshold filter 408 may discard the received irradiance data if it varies by a predetermined amount from the estimated irradiance.

For example, in one embodiment, when the measured irradiance at the PV system 304 is less than 75% of the estimated irradiance, the threshold filter 408 will discard the irradiance data. In another embodiment, the threshold filter 408 will discard irradiance data that is less than 85% of the estimated irradiance. In one embodiment, the threshold below which the threshold filter 408 discards the irradiance data is preset. Alternatively, the threshold may be defined by a user. In one embodiment, if the irradiance data is above the threshold, the analysis engine 400 continues processing the irradiance data. In another embodiment, if the measured irradiance data is above, or below, the estimated irradiance by more than a predetermined amount, the threshold filter 408 discards the irradiance data. In one embodiment, the predetermined amount is 25%. In another embodiment, the predetermined amount is 15%. In one embodiment, the threshold filter 408 passes the irradiance data to the curve fit filter 412 or another filter or module of the analysis engine 400.

Irradiance data that is significantly lower than the estimated irradiance may indicate cloud cover at the PV system 304, snow on PV strings 308, errors in environmental sensors 326, precipitation (such as rain or snow) or particulate matter in the air (including dust or pollution). Thus, when the difference between the irradiance data and the estimated irradiance is greater than the predetermined amount, the difference is not due to a problem with the irradiance sensor 324. By discarding the irradiance data, the threshold filter 308 ensures the analysis engine 300 does not attribute environmental variations to the irradiance sensor 324 and incorrectly calibrate the irradiance sensor 324.

The curve fit filter 412 receives the irradiance data measured by the irradiance sensor 324. In one embodiment, the curve fit filter 412 receives the irradiance data from the threshold filter 408. Optionally, in another embodiment, the curve fit filter 412 receives the irradiance data directly from the irradiance sensor 324.

The curve fit filter 412 compares or fits the irradiance data to a curve. Irradiance data that varies by more than a pre-set threshold is discarded by the curve fit filter 412. In one embodiment, the curve fit filter 412 discards irradiance data that has a low quality fit to a second order polynomial curve. Other mathematical techniques may be used for fitting the irradiance data to a curve. In this manner, the curve fit filter 412 can discard irradiance data that may be affected by environmental conditions (such as cloud cover) at the PV system 304. According to the invention, the curve fit filter 412 improves operation of the analysis engine 400 by taking into consideration current conditions at the PV system 304 such that the analysis engine 400 does not unnecessarily recalibrate the irradiance sensor 324 or generate unnecessary reports from the report module 424. More specifically, the curve fit filter 412 improves operation of the analysis engine 400 as well as the PV system 304 by preventing improper recalibration of the irradiance sensor 324 and/or expenses (such as labor and parts) associated with unnecessary travel, inspection, and service of an irradiance sensor 324 that does not require recalibration or service.

In one embodiment, the curve fit filter 412 analyzes the irradiance data within a time block of a predetermined length. For example, the curve fit filter 412 may analyze the irradiance data in a 1-hour time block. In another embodiment, the irradiance data is analyzed in 2-hour time blocks. The length of each time block may be predefined or entered by a user.

The correlation filter 416 compares measured irradiance data from the irradiance sensor 324 to the estimated irradiance received from the irradiance estimator 404. The correlation filter 416 discards irradiance data that deviates by more than a predetermined amount from the estimated irradiance. In this manner, the correlation filter 416 may further filter the irradiance data and reject irradiance data that may vary from the estimated irradiance due to an environmental condition, such as cloud cover at the PV system 304. Similar to the curve fit filter 412, the correlation filter 416 may analyze the irradiance data within a time block of a predetermined length, such as a 1-hour time block. In another embodiment, the irradiance data is analyzed in 2-hour time blocks. The length of each time block may be predefined or entered by a user.

The correlation filter 416 provides an improvement in operation of a PV system 304 by preventing erroneous reports for irradiance sensors 324 that are not malfunctioning which would otherwise be generated by the report module 424. Further, by rejecting irradiance data due to an environmental condition, the correlation filter 416 prevents unnecessary trips by service technicians to a PV system 304 and, accordingly, improves the efficiency and reduces expense associated with operation of the PV system 304.

In one embodiment, the correlation filter 416 receives the measured irradiance data from one or more of the threshold filter 408 and the curve fit filter 412. Optionally, the correlation filter 416 receives the irradiance data before one or more of the threshold and curve fit filters 408, 412. One of skill in the art will appreciate that the measured irradiance data may be processed by filters 408, 412, 416 in any order although (for simplicity) threshold filter 408 was described first.

The correction factor module 420 receives irradiance data measured by the irradiance sensor 324 that has passed filters 408, 412, 416. The correction factor module 420 then determines an irradiance weighted average associated with the irradiance sensor 324. The irradiance weighted average is defined as the ratio:

$$\text{Irradiance weighted average} = \frac{\sum (b_t \times M_t)}{\sum (b_t)}$$

where:
- $b_t$ is the estimated irradiance received from the irradiance estimator 404; and
- $M_t$ is the irradiance measured by the irradiance sensor 324 received from the correlation filter 416.

In this manner, the remaining data points $M_t$ from the irradiance sensor 324 (which were not rejected by one or more of the filters 408-416) are compared to the estimated irradiance, or blue sky model $b_t$. The correction factor module 420 may then save the irradiance weighted average to memory 220.

The irradiance weight average can be used as a correction factor to adjust raw irradiance data received from irradiance sensor 324. For example, the irradiance weight average may be used by a PV monitoring system to adjust the irradiance data measured by the irradiance sensor 324. In this manner, the accuracy of PV monitoring systems may be improved.

Due to the extensive filtering performed by filters 408, 412, 416, a few days, or possibly weeks, of measurements from the irradiance sensor 324 may be required to gather enough data for an effective irradiance weighted average suitable for use as a correction factor. Because degradation and soiling of irradiance sensors 324 is a relatively slow process, the remote calibration system 200 may analyze the data from the irradiance sensor 324 substantially continuously daily, weekly, monthly, or annually. Optionally, the correction factor module 420 may analyze historical data of an irradiance sensor 324 retrieved from memory that is compared to historical estimated irradiance generated by the irradiance estimator 404. In this manner, the remote calibration system 200 may be used to compensate for seasonal variations that may not be directly measurable or understood, such as air pollution that may vary due to nearby agricultural, industrial, or other sources.

The report module 424 may use information from one or more of the irradiance estimator, the correction factor module 420, and sensors 314, 318, 324, 326 of the PV system 304 to generate reports. The reports can include user interfaces or display images associated with the performance of the irradiance sensor 324. The report system is operable to provide information about the status of the PV system and performance of components of the PV system. In one embodiment, the report system can generate a report including information about the operation of an irradiance sensor associated with the PV system. The report can include information about the accuracy of the irradiance sensor, or error in data received from the irradiance sensor.

A report may include information about the irradiance sensor 324 such as: a new correction factor, a previous correction factor, a rate of change of the correction factor, a manufacture date, an installation date, and a date of last calibration. Optionally, the report may include a graph or chart of the irradiance data compared to the thresholds used by one or more of filters 408, 412, 416. The report may also compare the irradiance sensor 324 to one or more other irradiance sensors at the PV system 304 or other PV systems. Additionally, the report may be modified by the user. For example, the user can remove information displayed in one user interface to emphasize other information. A report may also include information from the output sensors 314, 318.

In one embodiment, the report module 424 can generate alarms. Alarms are a sub-set of reports generated by the report module 424. The report module can generate an alarm when a component of the PV system needs attention (on-site inspection) or is out of calibration by more than a predetermined amount. The report module 424 may generate an alarm when an irradiance sensor is improperly oriented. Additionally, the report module 424 may send an alarm when data from an irradiance sensor includes an error that is greater than a predetermined amount.

The reports generated by the report module 424 can be presented to a user in one or more graphs or display images displayed in a graphical user interface and displayed on an output device 215, such as a display. The format and information presented by the report module 424 in the display images may be altered by a user to show specific periods of time for one or more irradiance sensors of a PV system 204. Further, a user can request a report about the performance of one or more irradiance sensors at any time. The report module 424 may also retrieve data from one or more of the irradiance estimator 404 and filters 408, 412, 416 to generate reports.

In one embodiment, the report module 424 can adjust settings (or thresholds) used to determine when to send a report or an alarm. More specifically, the report module 424 can modify the settings to account for the irradiance weighted average.

In one embodiment, when the irradiance weighted average (or irradiance correction factor) for an irradiance sensor 324 exceeds a predetermined amount, the report module 424 may generate a report. The report may indicate that the irradiance sensor 324 should be calibrated, inspected, or replaced. Thus, in one embodiment, if the irradiance weighted average indicates that the irradiance sensor 324 is more than a predetermined first amount out of calibration, the report module 424 may generate a report indicating that the irradiance sensor 324 requires calibration. In one embodiment, the first amount is about 3%.

If the irradiance weighted average indicates the sensor 324 is more than a predetermined second mount out of calibration, the irradiance sensor 324 may be damaged or out of alignment. Thus, the report can indicate the irradiance sensor 324 should be inspected. In one embodiment, the second amount is about 10%.

If the irradiance weighted average of the irradiance sensor 324 changes at more than a predetermined rate, the irradiance sensor may have been damaged. For example, if the irradiance weighted average increases generally linearly from a first amount at a first time to a second amount at a second time and then remains substantially constant at the second amount at a third time, the irradiance sensor 324 may have moved out of level or may have been damaged, such as by impact.

The analysis engine 400 thus provides many benefits. The analysis engine 400 prevents or reduces unnecessary inspection and maintenance of an irradiance sensor 324 by determining the irradiance weighted average (or irradiance correction factor) for an irradiance sensor 324. Because the correction factor may be used to adjust raw sensor data received from the irradiance sensor 324, performance of the PV system 304 may be monitored without costly inspection or maintenance by a technician. In some embodiments, the analysis engine 400 can determine the accuracy of raw sensor data from an irradiance sensor 324 without adding additional sensors or other instruments to the PV system. Thus, the analysis engine 400 can use data supplied by existing sensors to calibrate and remotely monitor the performance of the irradiance sensor.

Another benefit is that the analysis engine 400 can determine that alignment of the irradiance sensor 324 is incorrect. More specifically, and as described above, the analysis engine 400 can determine the irradiance sensor 324 is improperly aligned (such as by not being level) when the irradiance weighted average for the irradiance sensor 324 increases during two or more measurements but subsequently does not increase.

The analysis engine 400 can also determine that the irradiance sensor 324 is improperly aligned by analyzing differences between an estimated irradiance from the irradiance estimator 404 and the measured irradiance from the irradiance sensor at various times of a day. More specifically, when an irradiance sensor 324 is not level, the irradiance sensor 324 may be oriented toward the sun for part of a day and away from the sun at another period during the day. During the period of the day when the irradiance sensor 324 is oriented toward the sun, the measured irradiance may be about equal to, or greater than, the estimated irradiance. However, at other times of the day in which the irradiance sensor is oriented away from the sun, the measured irradiance will be less than the estimated irradiance. Accordingly, the analysis engine 400 can determine the irradiance sensor 324 is improperly aligned. Additionally, irradiance data generated by the irradiance sensor will vary throughout each day and cannot be corrected with data from the correction factor module 420. Because of this, the report module 424 can generate a report indicating that the data from the irradiance sensor is inaccurate due to improper alignment of the irradiance sensor 324.

By determining a reason the measured irradiance from the irradiance sensor 324 does correspond to the data from the irradiance estimator 404, the time required for a technician to service the irradiance sensor 324 may be decreased. Further, the technician may be better prepared for the service call and may be able to bring parts required for the service call. Determining a reason for a difference between measured and estimated irradiance and also prevents unnecessary procurement of replacement irradiance sensors, for example, when the technician can correct the orientation of the irradiance sensor 324.

Figure 5:
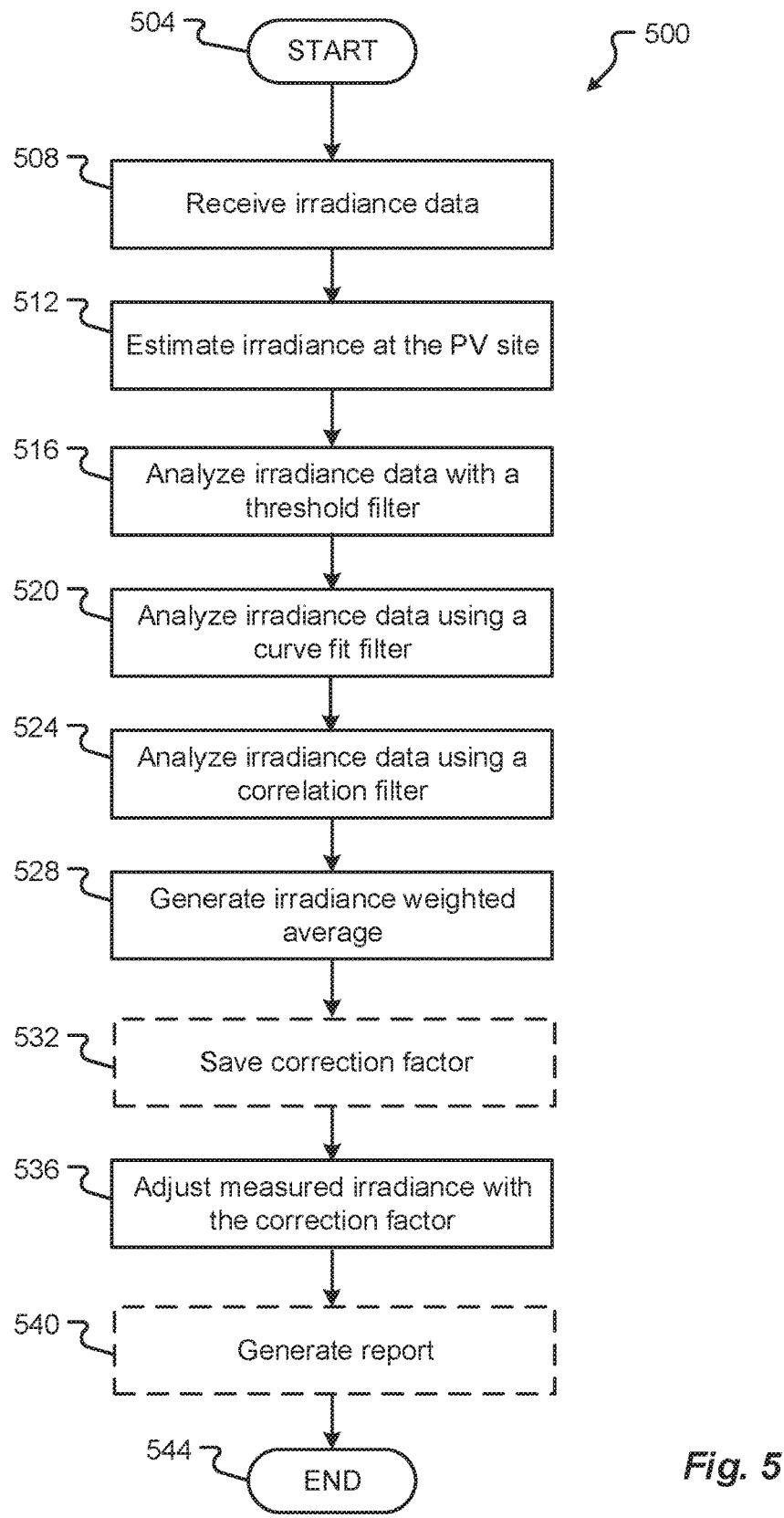
FIG. 5 illustrates a flow diagram of a remote calibration method of an embodiment of the invention.

Referring now to FIG. 5, an embodiment of a remote calibration method 500 of the invention is illustrated. While a general order for the operations of method 500 is shown in FIG. 5, the method 500 can include more or fewer operations or can arrange the order of the operations differently than those shown in FIG. 5. Further, two or more operations may be combined into one operation. Further, although the operations of the method 500 may be described sequentially, many of the operations may in fact be performed in parallel or concurrently. Generally, the method 500 starts with a start operation 504 and ends with an end operation 544. At least some of the operations of method 500 can be executed as a set of computer-executable instructions executed by a data-processing system and encoded or stored on a computer readable medium. Hereinafter, the method 500 shall be explained with reference to the systems, components, modules, software, data structures, user interfaces, etc. described in conjunction with FIGS. 1-4.

At operation 508, the remote calibration system 200 receives irradiance data from an irradiance sensor 324 of a PV system 304. The irradiance estimator 404 generates an estimated irradiance for the PV system 304 using a blue-sky model in operation 512. The remote calibration system 200 may use a network 120 to connect to a remote source operable to calculate an estimate irradiance based on the location of the PV system. The irradiance estimator 404 may adjust the estimated irradiance using a seasonal correction factor. The estimated irradiance may also be adjusted by the irradiance estimator 404 to account for one or more environmental conditions at the PV system 304. For example, the irradiance estimator 404 may use data from environmental sensors 326 of the PV system 304 or other sources, such as a local weather service, to account for the environmental conditions.

Optionally, the irradiance estimator 404 can use data from one or more of the output sensors 314, 318 to adjust the estimated irradiance. More specifically, in one embodiment, the irradiance estimator 404 receives data related to DC power output from a combiner from output sensor 314 or AC power output by an inverter 316 from output sensor 318. The data from output sensors 314, 318 may indicate that the PV system 304 is generating a different amount of power than expected based on the estimated irradiance from the irradiance estimator 404. The irradiance estimator 404 can then adjust the estimated irradiance to account for the power output data received from the output sensors 314, 318.

In operations 516, 520, 524, the irradiance data from the irradiance sensor 324 is filtered. The threshold filter 408, curve fit filter 412, and correlation filter 416 discard irradiance data that indicates environmental factors are causing a decrease in measured irradiance rather than an error of the irradiance sensor 324. In this manner, method 500 prevents unnecessary reports which may otherwise be generated when the irradiance sensor 324 is functioning properly, or when a correction factor may be applied to the raw irradiance data. Accordingly, method 500 improves operation of a PV system 304 by preventing unnecessary service trips by technicians to inspect or service an irradiance sensor 324. The irradiance data may be processed by filters 408, 412, 416 in any desired order.

At operation 528, the correction factor module 420 generates an irradiance weighted average for the irradiance sensor 324. As described above, the correction factor module 420 compares remaining data points $M_t$ that were not rejected by filters 408, 412, 416 received from the irradiance sensor 324 to the estimated irradiance, or blue sky model $b_t$ generated by the irradiance estimator 404.

The irradiance weighted average may then be saved to memory in operation 532. Subsequently, the irradiance weighted average may be used as a correction factor to adjust irradiance data measured by the irradiance sensor 324 in operation 536. The irradiance weighted average can also be used to adjust logic of a report module 424. More specifically, the report module 424 can take into account the irradiance weighted average of the irradiance sensor. Accordingly, in one embodiment, when irradiance data from the irradiance sensor 324 may be used after adjustment by the irradiance weighted average, the report module 424 will not generate a report indicating that the irradiance sensor 324 is out of calibration.

The remote calibration system 200 may generate one or more reports using the report module 424 in operation 540. When the irradiance weighted average exceeds a predetermined threshold, the report module 424 can send an alert to a user indicating that the irradiance sensor 324 should be inspected and/or calibrated. Optionally, when the irradiance weighted average for the irradiance sensor 324 changes over a predetermined period of time by more than a predetermined amount, the report module 424 may send an alert indicating that the irradiance sensor may be damaged or out of alignment. The alert may recommend inspection of the irradiance sensor 324.

Optionally, the report module 424 can alter a report associated with the irradiance sensor 324. For example, in one embodiment, the report module 424 can adjust a report to indicate the irradiance weighted average for the irradiance sensor or that data from the irradiance sensor 324 can be used after adjustment with the irradiance weighted average. In this manner, the report module 424 prevents reports which improperly indicate that the irradiance sensor 324 requires inspection or is providing inaccurate data.

Method 500 may then End (operation 544) or return to operation 508.

One of skill in the art will appreciate that method 500 may loop any number of times from operation 540 back to operation 508. In one embodiment of the invention, method 500 repeats at least 1 time per hour. In another embodiment, method 500 repeats approximately every 15 minutes. In still another embodiment, method 500 repeats every 5 minutes. Further, the method 500 may use historical data received over any period of time in which the irradiance sensor 324 has collected irradiance data at the PV system 304.

Figure 6:
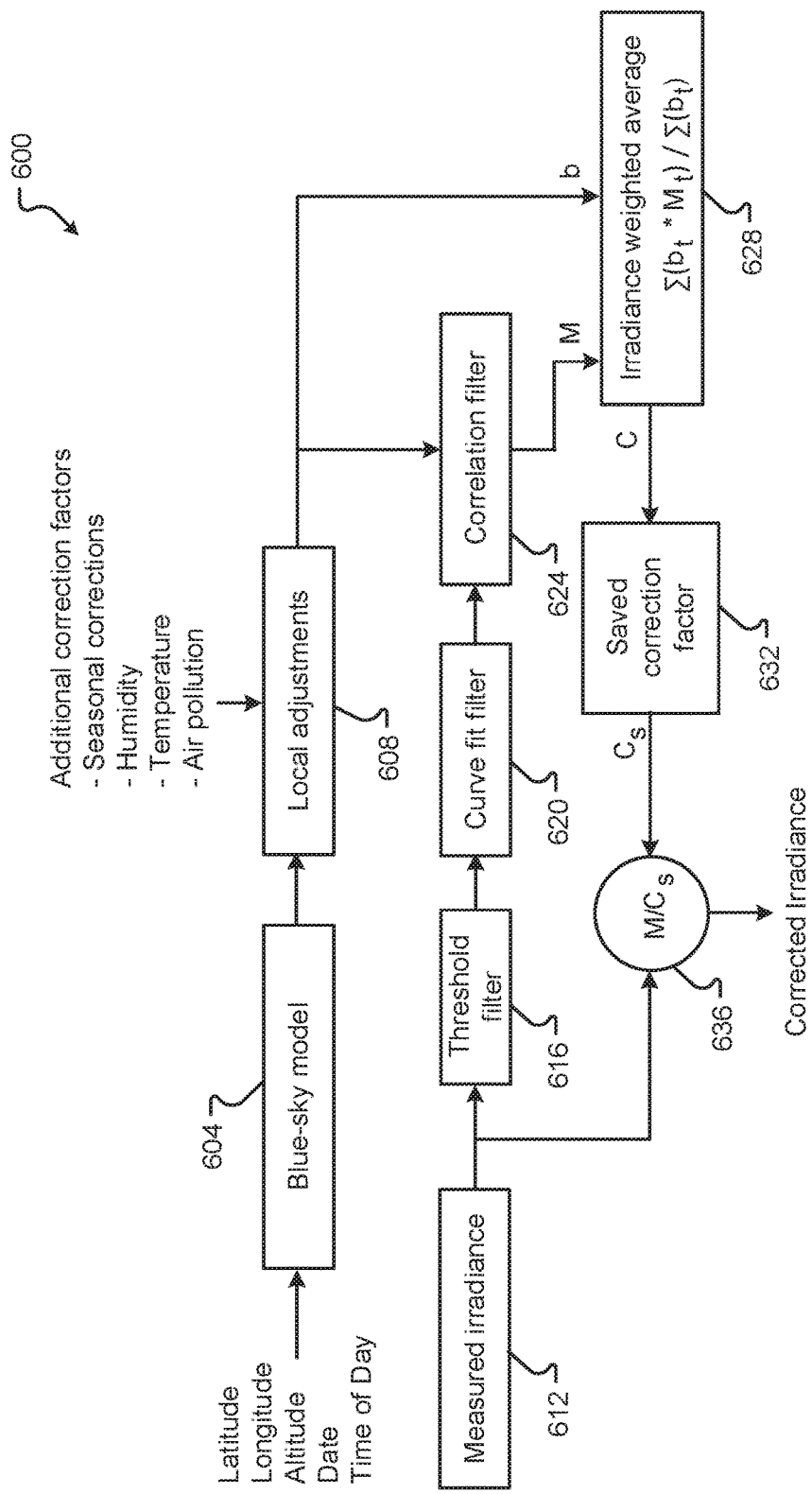
FIG. 6 illustrates another embodiment of a remote calibration method of the invention.

Referring now to FIG. 6, an embodiment of another remote calibration method 600 of the invention is illustrated. Method 600 is similar to method 500. Accordingly, the operations of the method 600 are generally shown in FIG. 6 and method 600 can include more or fewer operations or can arrange the order of the operations differently than those shown in FIG. 6. Further, two or more operations may be combined into one operation and although the operations are illustrated in one sequence, many of the operations may in fact be performed in parallel or concurrently. At least some of the operations of method 600 can be executed as a set of computer-executable instructions executed by a data-processing system and encoded or stored on a computer readable medium. The method 600 may be performed using the systems, components, modules, software, data structures, user interfaces, etc. described in conjunction with FIGS. 1-5.

More specifically, at operation 604, the remote calibration system 200 generates an estimated irradiance for a PV system 304. Optionally, the remote calibration system 200 receives the estimated irradiance from a remote blue-sky calculator, for example, using network 120. In one embodiment, the irradiance estimator 404 of the analysis engine 400 generates the estimated irradiance for the PV system 304.

The remote calibration system 200 may optionally adjust the estimated irradiance at operation 608 using corrections factors. The correction factors may include one or more of a seasonal correction, a humidity correction, a temperature correction, and a correction for air pollution. The system 200 may use data from an environmental system 326 of the PV system 304 to determine the correction factors to use with the estimate irradiance.

In operation 612 the remote calibration system 200 receives measured irradiance data from an irradiance sensor 324 of the PV system 304. The remote calibration system 200 then filters the measured irradiance data using one or more of a threshold filter 408, curve fit filter 412, and correlation filter 416 in operations 616, 620, and 624, respectively.

Using the estimated irradiance data and the filtered measured irradiance data, the remote calibration system 200 determines an irradiance weighted average in operation 628. As described herein, the correction factor module 420 compares remaining data points $M_t$ that were not rejected by filters 408, 412, 416 received from the irradiance sensor 324 to the estimated irradiance, or blue sky model $b_t$ generated by the irradiance estimator 404 (or received from network 120) in operation 628.

The irradiance weighted average may then be saved to memory in operation 632. Subsequently, the irradiance weighted average may be used to adjust irradiance data measured by the irradiance sensor 324 in operation 636.

The irradiance weighted average (or correction factor) may also be used by the report module 424. More specifically, the report module 424 may generate a report indicating the irradiance weighted average associated with the irradiance sensor. Additionally, or alternatively, the report module 424 can adjust an alert threshold of the irradiance sensor to prevent generation of a report when data from the irradiance sensor is useable after correction with the correction factor.

In one embodiment, the report module 424 may use the irradiance weighted average to determine that the irradiance sensor 324 should be inspected. The report module 424 may determine a cost associated with sending a technician to the irradiance sensor before generating an inspection required report. Optionally, if the cost of sending the technician to the irradiance sensor is greater than a predetermined amount, the report module will not send the inspection required report.

Systems and methods of monitoring PV systems are more accurate when parameters are tuned (or calibrated) with systems and methods of the present invention. The comparison of the measured irradiance at the site of a PV system 304 to existing model performance allows remote calibration of irradiance sensors 324 without the cost associated with removing and replacing irradiance sensors for factory calibration. Further, irradiance sensors may be remotely calibrated continuously, improving the quality of the irradiance data used by other systems to monitor the performance of PV systems, such as those that used to identify and quantify losses. Additionally, the systems and methods of the present invention improve efficiency of PV systems by decreasing the frequency of trips by technicians to inspect irradiance sensors.

The foregoing discussion has been presented for purposes of illustration and description. The foregoing is not intended to limit the disclosure to the form or forms disclosed herein. In the foregoing Detailed Description for example, various features of the invention are grouped together in one or more aspects, embodiments, and/or configurations for the purpose of streamlining the disclosure. The features of the aspects, embodiments, and/or configurations of the invention may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate embodiment of the invention.

The invention, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the invention. The invention, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Furthermore, while the exemplary aspects, embodiments, options, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

In the foregoing description, for the purposes of illustration, methods were described in a particular order. It should be appreciated that in alternate embodiments, the methods may be performed in a different order than that described, and that changes, additions, and omissions to the order of the methods can occur without materially affecting the operation of the disclosed embodiments, configurations, and aspects of the invention. It should also be appreciated that the methods described above may be performed at least in part by hardware components. Additionally, some operations or portions of the methods described herein may be embodied in sequences of machine-executable instructions, which may be used to cause a machine, such as a general-purpose or special-purpose processor or logic circuits programmed with the instructions, to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Optionally, the systems and methods of this invention can be implemented in conjunction with a special purpose computer, a special purpose data-processing system, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this invention. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this invention is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this invention can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Moreover, though the description has included description of one or more aspects, embodiments, and/or configurations and certain variations and modifications, other variations, combinations, and modifications are within the scope of the invention, e.g., as may be within the skill and knowledge of those in the art, after understanding the invention. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. While the invention has been discussed with respect to various embodiments, it shall be understood that various other changes and modifications to the invention can be made in accordance with the scope of the claims appended hereto.

What is claimed is:

1. A method of analyzing and calibrating an irradiance sensor of a photovoltaic (PV) system, comprising:
    estimating a value of irradiance received at the PV system for a time and a date and based on a latitude, a longitude, and an elevation of the PV system;
    measuring a value of irradiance received at the PV system for the time and the date by the irradiance sensor;
    filtering the measured irradiance value using one or more of a threshold filter, a curve fit filter, and a correlation filter to generate a filtered irradiance value;
    generating an irradiance weighted average for the irradiance sensor by comparing the filtered irradiance value to the estimated irradiance value; and
    adjusting values of irradiance measured by the irradiance sensor with the irradiance weighted average to compensate for error of the irradiance sensor.

2. The method of claim 1, wherein the value of irradiance received at the PV system is estimated using a blue-sky model.

3. The method of claim 1, wherein the adjusted values of irradiance from the irradiance sensor are used by a PV monitoring system to improve an output of the PV monitoring system.

4. The method of claim 1, wherein filtering the measured irradiance value comprises discarding a measured irradiance value that varies from an estimated irradiance value by more than a predetermined amount.

5. The method of claim 1, wherein generating the irradiance weighted average comprises comparing filtered irradiance values $M_t$ from the irradiance sensor to estimated irradiance values $b_t$ using the formula:

$$\frac{\sum (b_t * M_t)}{\sum (b_t)}.$$

6. A system for analyzing and calibrating an irradiance sensor of a photovoltaic (PV) system, comprising:
    a memory; and
    a processor in communication with the memory, the processor programmed to:
        receive an estimated amount of irradiance received by the PV system, wherein the estimated irradiance amount is determined for a time and a date and is based on a latitude, a longitude, and an elevation of the PV system;
        receive an amount of irradiance measured by the irradiance sensor eat the PV system for the time and the date;
        filter the measured irradiance amount by discarding the measured irradiance amount if the measured irradiance amount varies from the estimated irradiance amount by more than a predetermined value to generate a filtered irradiance amount;
        generate an irradiance weighted average for the irradiance sensor by comparing the filtered irradiance amount to the estimated irradiance amount, and
        adjust amounts of irradiance measured by the irradiance sensor with the irradiance weighted average to compensate for error of the irradiance sensor.

7. The system of claim 6, further comprising:
    a photovoltaic string to convert sunlight into electrical energy;
    a combiner to combine DC power from a plurality of photovoltaic strings;
    an inverter for converting DC power from a plurality of combiners into AC power; and
    a sensor to detect environmental conditions at the PV system.

8. The system of claim 6, wherein the processor is further programmed to:
    modify a report module using the irradiance weighted average.

9. The system of claim 8, wherein modifying the report module prevents generation of a report associated with the irradiance sensor when error of the irradiance sensor can be corrected using the irradiance weighted average.

10. The system of claim 8, wherein the processor is further programmed to:
    generate a report from the report module when error of the irradiance sensor cannot be corrected with the irradiance weighted average.

11. The system of claim 10, wherein the report module generates a report when the irradiance weighted average indicates the irradiance sensor is out of calibration by greater than 3 percent.

12. The system of claim 6, wherein the processor is further programmed to:
    determine a reason the measured irradiance amount from the irradiance sensor is different from the estimated irradiance amount.

13. The system of claim 12, wherein the processor uses the irradiance weighted average to determine at least one of:
    a) the irradiance sensor is damaged; and
    b) the irradiance sensor is out of alignment.

14. The system of claim 13, further comprising:
    determining the irradiance sensor is damaged when the irradiance weighted average changes at greater than a predetermined rate; and
    determining the irradiance sensor is out of alignment when a difference between the measured irradiance amount and the estimated irradiance amount varies based on a position of the sun.

15. The system of claim 13, wherein the processor is further programmed to:
    generate a report with a report module after determining the irradiance sensor is damaged or is out of alignment, the report indicating that the irradiance sensor needs on-site inspection.

16. The system of claim 6, wherein measured irradiance amounts from the irradiance sensor that have been adjusted with the irradiance weighted average are used by a PV monitoring system to improve an output of the PV monitoring system.

17. A non-transitory computer readable medium having stored thereon computer-executable instructions executable by a processor of a remote calibration system, the computer-executable instructions causing the processor to execute a method of analyzing performance of an irradiance sensor of a photovoltaic (PV) system, comprising:
    an instruction to estimate a value of irradiance received by the PV system at a time and a date and based on a location and an elevation of the PV system using a blue-sky model;
    an instruction to receive a value of irradiance measured by the irradiance sensor of the PV system at the time and the date;

an instruction to filter the measured irradiance value using the estimated irradiance value to generate a filtered irradiance value; and an instruction to generate an irradiance weighted average for the irradiance sensor by comparing the filtered irradiance value to the estimated irradiance value, wherein the measured irradiance value from the irradiance sensor is adjusted by the irradiance weighted average to compensate for error of the irradiance sensor and to generate an adjusted irradiance value, and wherein the adjusted irradiance value is used by a PV monitoring system.

18. The non-transitory computer readable medium of claim 17, wherein the instruction to filter further comprises:

discarding the measured irradiance value when it varies from the estimated irradiance value by more than a predetermined amount.

19. The non-transitory computer readable medium of claim 17, further comprising an instruction to generate a report to at least one of:

inspect the irradiance sensor; and calibrate the irradiance sensor.

20. The non-transitory computer readable medium of claim 17, further comprising:

an instruction prevent generation of a report when measured irradiance values from the irradiance sensor can be corrected with the irradiance weighted average.

* * * * *